(12) United States Patent
Desmond, III et al.

(10) Patent No.: US 6,332,892 B1
(45) Date of Patent: Dec. 25, 2001

(54) MEDICAL DEVICE WITH ONE OR MORE HELICAL COILS

(75) Inventors: Joseph P. Desmond, III; Doug Walls, both of Bloomington, IN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/260,596

(22) Filed: Mar. 2, 1999

(51) Int. Cl.$^7$ ........................................ A61F 2/06

(52) U.S. Cl. ........................................ 623/1.15; 606/198

(58) Field of Search ............................ 606/198; 604/588, 604/8, 10, 9, 280; 600/135, 139, 143, 144; 623/12, 14, 1.11, 1.12–1.16

(56) References Cited

U.S. PATENT DOCUMENTS

| | | | |
|---|---|---|---|
| Re. 31,873 | 4/1985 | Howes | 128/674 |
| 191,775 | 6/1877 | Parsons . | |
| 256,590 | 4/1882 | Pfarre . | |
| D. 272,651 | 2/1984 | Marhurkar | D24/54 |
| 386,603 | 7/1888 | Parsons . | |
| 559,620 | 5/1896 | Shearer . | |
| 1,211,928 | 1/1917 | Fisher . | |
| 2,247,369 | 9/1941 | Davis | 128/349 |
| 3,087,493 | 4/1963 | Schossow | 128/351 |
| 3,314,340 | 4/1967 | Alley et al. | 128/350 |
| 3,359,974 | 12/1967 | Khalil | 128/2.05 |
| 3,394,705 | 7/1968 | Abramson | 128/349 |
| 3,437,088 | 4/1969 | Bielinski | 128/2 |
| 3,485,234 | 12/1969 | Stevens | 128/2 |
| 3,593,713 | 7/1971 | Bogoff et al. | 128/246 |
| 3,612,050 | 10/1971 | Sheridan | 128/214.4 |
| 3,633,579 | 1/1972 | Alley et al. | 128/214.4 |
| 3,726,281 | 4/1973 | Norton et al. | 128/349 R |

(List continued on next page.)

FOREIGN PATENT DOCUMENTS

| | | |
|---|---|---|
| 1092927 | 1/1981 | (CA) . |
| 1150122 | 7/1983 | (CA) . |
| 1167727 | 5/1984 | (CA) . |
| 1193508 | 9/1985 | (CA) . |
| 1219785 | 3/1987 | (CA) . |
| 1225299 | 11/1987 | (CA) . |
| 2259865 | 6/1974 | (DE) . |
| 3112762 C2 | 1/1983 | (DE) . |
| 35 17 813 A | 11/1986 | (DE) . |
| 37 40 288 C | 4/1989 | (DE) . |

(List continued on next page.)

OTHER PUBLICATIONS

Bard Access Systems Vas–Cath Incorporated Catalog (date unknown).
Cook Critical Care Catalog, "Products for Dialysis" pp. 3–15 (1989).
Cook Critical Care Catalog, "Uldall Double Lumen Hemodialysis Catheter Trays" (date unknown).
Horizon Medical Products Catalog (date unknown).
McIntosh, et al. J.A.M.A. 169(8): 137–8 (1959).
MEDCOMP Catalog, "Hemodialysis Products" pp. 1–11, 14–16, 19–27, 30–36 (date unknown).

(List continued on next page.)

*Primary Examiner*—Henry J. Recla
*Assistant Examiner*—Tan-Uyen T. Ho
(74) *Attorney, Agent, or Firm*—Testa, Hurwitz & Thibeault, LLP (57) ABSTRACT

Medical devices, such as drainage stents, having coiled structures are useful in draining body fluids. A medical device has a first elongated section with a first cross-sectional area and a second elongated section with a second cross-sectional area. The second elongated section extends from the first elongated section. The second cross-sectional area is smaller than the first cross-sectional area. The second elongated section is or has at least one coiled structure with a plurality of turns, such as a helical coil tail.

13 Claims, 5 Drawing Sheets

U.S. PATENT DOCUMENTS

| | | | |
|---|---|---|---|
| 3,746,003 | 7/1973 | Blake et al. | 128/349 B |
| 3,788,326 | 1/1974 | Jacobs | 128/305 |
| 3,828,767 | 8/1974 | Spiroff | 128/2.05 |
| 3,902,492 | 9/1975 | Greenhalgh | 128/241 |
| 3,906,954 | 9/1975 | Baehr et al. | 128/305 |
| 3,920,023 | 11/1975 | Dye et al. | 128/347 |
| 3,995,623 | 12/1976 | Blake et al. | 128/2.06 E |
| 4,004,588 | 1/1977 | Alexander | 128/241 |
| 4,037,599 | 7/1977 | Raulerson | 128/214.4 |
| 4,065,264 | 12/1977 | Lewin | 23/258.5 BH |
| 4,069,814 | 1/1978 | Clemens | 128/2 F |
| 4,096,860 | 6/1978 | McLaughlin | 128/214.4 |
| 4,099,528 | 7/1978 | Sorenson et al. | 128/214.4 |
| 4,100,246 | 7/1978 | Frisch | 264/230 |
| 4,129,129 | 12/1978 | Amrine | 128/214 |
| 4,134,402 | 1/1979 | Marhurkar | 128/214 |
| 4,138,288 | 2/1979 | Lewin | 195/1.8 |
| 4,138,457 | 2/1979 | Rudd et al. | 264/500 |
| 4,144,884 | 3/1979 | Tersteegen et al. | 128/214.4 |
| 4,149,535 | 4/1979 | Volder | 128/214.4 |
| 4,168,703 | 9/1979 | Kenigsberg | 128/748 |
| 4,173,981 | 11/1979 | Mortensen | 128/348 |
| 4,180,068 | 12/1979 | Jacobsen et al. | 128/214 R |
| 4,182,739 | 1/1980 | Curtis | 422/47 |
| 4,183,961 | 1/1980 | Curtis | 424/366 |
| 4,202,332 | 5/1980 | Tersteegen et al. | 128/214.4 |
| 4,203,436 | 5/1980 | Grimsrud | 128/214 R |
| 4,204,541 * | 5/1980 | Kapitanov | 606/223 |
| 4,212,304 | 7/1980 | Finney | 128/349 R |
| 4,217,895 | 8/1980 | Sagae et al. | 128/214.4 |
| 4,223,676 | 9/1980 | Wuchinich et al. | 128/276 |
| 4,236,520 | 12/1980 | Anderson | 128/348 |
| 4,239,042 | 12/1980 | Asai | 128/214.4 |
| 4,257,416 | 3/1981 | Prager | 128/214 R |
| 4,270,535 | 6/1981 | Bogue et al. | 128/214.4 |
| 4,307,723 | 12/1981 | Finney | 604/8 |
| 4,327,722 | 5/1982 | Groshong et al. | 128/214.4 |
| 4,334,327 | 6/1982 | Lyman et al. | 3/1 |
| 4,385,631 | 5/1983 | Uthmann | 604/284 |
| 4,403,983 | 9/1983 | Edelman et al. | 604/43 |
| 4,405,313 | 9/1983 | Sisley et al. | 604/43 |
| 4,405,314 | 9/1983 | Cope | 604/51 |
| 4,406,656 | 9/1983 | Hattler et al. | 604/280 |
| 4,413,989 | 11/1983 | Schjeldahl et al. | 604/96 |
| 4,419,094 | 12/1983 | Patel | 604/93 |
| 4,443,333 | 4/1984 | Marhurkar | 210/87 |
| 4,451,252 | 5/1984 | Martin | 604/43 |
| 4,456,000 | 6/1984 | Schjeldahl et al. | 128/1 D |
| 4,484,585 | 11/1984 | Baier | 128/748 |
| 4,493,696 | 1/1985 | Uldall | 604/43 |
| 4,504,264 | 3/1985 | Kelman | 604/22 |
| 4,531,933 | 7/1985 | Norton et al. | 604/8 |
| 4,540,402 | 9/1985 | Aigner | 604/44 |
| 4,543,087 | 9/1985 | Sommercorn et al. | 604/43 |
| 4,559,046 | 12/1985 | Groshong et al. | 604/282 |
| 4,563,170 | 1/1986 | Aigner | 604/5 |
| 4,568,329 | 2/1986 | Marhurkar | 604/43 |
| 4,568,338 | 2/1986 | Todd | 604/281 |
| 4,581,012 | 4/1986 | Brown et al. | 604/43 |
| 4,583,968 | 4/1986 | Marhurkar | 604/43 |
| 4,596,548 | 6/1986 | DeVries et al. | 604/4 |
| 4,601,697 | 7/1986 | Mammolenti et al. | 604/43 |
| 4,601,701 | 7/1986 | Mueller, Jr. | 604/83 |
| 4,608,993 | 9/1986 | Albert | 128/663 |
| 4,610,657 | 9/1986 | Densow | 604/8 |
| 4,619,643 | 10/1986 | Bai | 604/43 |
| 4,623,327 | 11/1986 | Marhurkar | 604/4 |
| 4,626,240 | 12/1986 | Edelman et al. | 604/43 |
| 4,641,652 * | 2/1987 | Hutterer et al. | 606/223 |
| 4,643,711 | 2/1987 | Bates | 604/4 |
| 4,643,716 | 2/1987 | Drach | 604/8 |
| 4,648,865 | 3/1987 | Aigner | 604/5 |
| 4,655,771 | 4/1987 | Wallstén . | |
| 4,666,426 | 5/1987 | Aigner | 604/5 |
| 4,671,795 | 6/1987 | Mulchin | 604/281 |
| 4,675,004 | 6/1987 | Hadford et al. | 604/44 |
| 4,682,978 | 7/1987 | Martin | 604/43 |
| 4,687,471 | 8/1987 | Twardowski et al. | 604/175 |
| 4,692,141 | 9/1987 | Marhurkar | 604/43 |
| 4,694,838 | 9/1987 | Wijayarthna et al. | 128/658 |
| 4,713,049 | 12/1987 | Carter | 604/8 |
| 4,722,725 | 2/1988 | Sawyer et al. | 604/27 |
| 4,732,152 | 3/1988 | Wallstén et al. . | |
| 4,737,146 | 4/1988 | Amaki et al. | 604/51 |
| 4,738,667 | 4/1988 | Galloway | 604/281 |
| 4,747,840 | 5/1988 | Ladika et al. | 604/281 |
| 4,753,640 | 6/1988 | Nichols et al. | 604/247 |
| 4,755,176 | 7/1988 | Patel | 604/280 |
| 4,769,005 | 9/1988 | Ginsburg et al. | 604/53 |
| 4,770,652 | 9/1988 | Marhurkar | 604/4 |
| 4,772,268 | 9/1988 | Bates | 604/174 |
| 4,773,432 | 9/1988 | Rydell | 128/772 |
| 4,776,841 | 10/1988 | Catalano | 604/43 |
| 4,787,884 | 11/1988 | Goldberg | 604/8 |
| 4,790,809 | 12/1988 | Kuntz | 604/8 |
| 4,790,810 | 12/1988 | Pugh, Jr. et al. | 604/8 |
| 4,795,439 | 1/1989 | Guest | 604/43 |
| 4,808,155 | 2/1989 | Marhurkar | 604/43 |
| 4,809,710 | 3/1989 | Williamson | 128/748 |
| 4,813,429 | 3/1989 | Eshel et al. | 128/736 |
| 4,813,925 | 3/1989 | Anderson, Jr. et al. | 604/8 |
| 4,820,262 | 4/1989 | Finney | 604/8 |
| 4,822,345 | 4/1989 | Danforth | 604/282 |
| 4,838,881 | 6/1989 | Bennett | 604/280 |
| 4,842,582 | 6/1989 | Marhurkar | 604/43 |
| 4,842,590 | 6/1989 | Tanabe et al. | 604/282 |
| 4,846,791 | 7/1989 | Hattler et al. | 604/43 |
| 4,846,814 | 7/1989 | Ruiz | 604/281 |
| 4,863,442 | 9/1989 | DeMello et al. | 604/282 |
| 4,874,360 | 10/1989 | Goldberg et al. | 604/8 |
| 4,887,996 | 12/1989 | Bengmark | 604/54 |
| 4,894,057 | 1/1990 | Howes | 604/280 |
| 4,895,561 | 1/1990 | Marhurkar | 604/43 |
| 4,913,683 | 4/1990 | Gregory | 604/8 |
| 4,931,037 | 6/1990 | Wetterman | 604/8 |
| 4,950,228 | 8/1990 | Knapp, Jr. et al. | 604/8 |
| 4,954,126 * | 9/1990 | Wallsten | 606/198 |
| 4,960,409 | 10/1990 | Catalano | 604/53 |
| 4,960,411 | 10/1990 | Buchbinder | 604/95 |
| 4,961,809 | 10/1990 | Martin | 156/294 |
| 4,963,129 | 10/1990 | Rusch | 604/8 |
| 4,973,301 | 11/1990 | Nissenkorn . | |
| 4,978,341 | 12/1990 | Niederhauser . | |
| 4,981,482 | 1/1991 | Ichikawa | 606/108 |
| 4,985,022 | 1/1991 | Fearnot et al. | 604/682 |
| 4,986,814 | 1/1991 | Burney et al. | 604/164 |
| 4,990,133 | 2/1991 | Solazzo | 604/8 |
| 4,994,071 * | 2/1991 | MacGregor | 623/1.15 |
| 4,995,863 | 2/1991 | Nichols et al. | 604/247 |
| 4,995,865 | 2/1991 | Gahara et al. | 604/43 |
| 4,995,868 | 2/1991 | Brazier | 604/105 |
| 4,998,919 | 3/1991 | Schnepp-Pesch et al. | 604/164 |
| 5,009,636 | 4/1991 | Wortley et al. | 604/43 |
| 5,013,296 | 5/1991 | Buckberg et al. | 604/44 |
| 5,019,102 | 5/1991 | Hoene | 623/12 |
| 5,026,377 | 6/1991 | Burton et al. . | |
| 5,029,580 | 7/1991 | Radford et al. | 128/207.14 |
| 5,041,083 | 8/1991 | Tsuchida et al. | 604/43 |
| 5,053,004 | 10/1991 | Markel et al. | 604/43 |
| 5,053,023 | 10/1991 | Martin | 604/280 |
| 5,057,073 | 10/1991 | Martin | 604/43 |

| | | |
|---|---|---|
| 5,061,275 | 10/1991 | Wallstén et al. . |
| 5,078,720 | 1/1992 | Burton et al. . |
| 5,116,309 | 5/1992 | Coll .......................................... 604/8 |
| 5,124,127 | 6/1992 | Jones et al. ............................ 422/46 |
| 5,129,910 | 7/1992 | Phan et al. ............................ 606/127 |
| 5,135,487 | 8/1992 | Morrill et al. .......................... 604/96 |
| 5,135,599 | 8/1992 | Martin et al. ........................ 156/294 |
| 5,141,502 | 8/1992 | Macaluso, Jr. ....................... 604/281 |
| 5,147,370 | 9/1992 | McNamara et al. . |
| 5,149,330 | 9/1992 | Brightbill .............................. 604/280 |
| 5,156,592 | 10/1992 | Martin et al. ........................... 604/43 |
| 5,156,596 | 10/1992 | Balbierz et al. ...................... 604/164 |
| 5,160,325 | 11/1992 | Nichols et al. ....................... 604/247 |
| 5,167,623 | 12/1992 | Cianci et al. ........................... 604/43 |
| 5,171,216 | 12/1992 | Dasse et al. ............................ 604/43 |
| 5,176,625 | 1/1993 | Brisson .................................... 604/8 |
| 5,176,626 | 1/1993 | Soehendra ............................... 604/8 |
| 5,178,803 | 1/1993 | Tsuchida et al. ...................... 264/23 |
| 5,188,593 | 2/1993 | Martin ..................................... 604/43 |
| 5,190,520 | 3/1993 | Fenton, Jr. et al. ................... 604/43 |
| 5,195,962 | 3/1993 | Martin et al. ........................... 604/43 |
| 5,197,951 | 3/1993 | Marhurkar ............................... 604/93 |
| 5,207,648 | 5/1993 | Gross ..................................... 604/164 |
| 5,209,723 | 5/1993 | Twardowski et al. ................. 604/43 |
| 5,211,627 | 5/1993 | William .................................. 604/82 |
| 5,221,253 | 6/1993 | Coll .......................................... 604/8 |
| 5,221,255 | 6/1993 | Marhurkar et al. ..................... 604/43 |
| 5,221,256 | 6/1993 | Marhurkar ............................... 604/43 |
| 5,224,953 | 7/1993 | Morgentaler . |
| 5,234,663 | 8/1993 | Jones et al. ............................. 422/46 |
| 5,240,677 | 8/1993 | Jones et al. ............................. 422/46 |
| 5,242,395 | 9/1993 | Maglinte ................................. 604/96 |
| 5,246,445 | 9/1993 | Yachia et al. . |
| 5,250,038 | 10/1993 | Melker et al. ........................ 604/264 |
| 5,261,979 | 11/1993 | Brill ........................................ 604/96 |
| 5,269,802 | 12/1993 | Garber ...................................... 604/8 |
| 5,275,597 | 1/1994 | Higgins et al. ........................ 606/33 |
| 5,279,560 | 1/1994 | Morrill et al. .......................... 604/96 |
| 5,282,784 | 2/1994 | Willard .................................... 604/8 |
| 5,292,305 | 3/1994 | Boudewijn et al. .................... 604/43 |
| 5,295,954 | 3/1994 | Sachse ..................................... 604/8 |
| 5,308,322 | 5/1994 | Tennican et al. ....................... 604/83 |
| 5,318,532 | 6/1994 | Frassica ................................... 604/96 |
| 5,324,274 | 6/1994 | Martin ................................... 604/248 |
| 5,330,449 | 7/1994 | Prichard et al. ...................... 604/282 |
| 5,338,311 | 8/1994 | Marhurkar ............................ 604/195 |
| 5,342,301 | 8/1994 | Saab ........................................ 604/96 |
| 5,342,387 | * 8/1994 | Summers ............................. 623/1.15 |
| 5,346,467 | 9/1994 | Coll .......................................... 604/8 |
| 5,346,471 | 9/1994 | Raulerson ............................... 604/43 |
| 5,348,536 | 9/1994 | Young et al. ........................... 604/43 |
| 5,354,263 | 10/1994 | Coll .......................................... 604/8 |
| 5,354,309 | 10/1994 | Schnepp-Pesch et al. . |
| 5,356,423 | 10/1994 | Tihon et al. . |
| 5,356,424 | * 10/1994 | Buzerak et al. ...................... 606/223 |
| 5,358,689 | 10/1994 | Jones et al. ............................. 422/46 |
| 5,360,397 | 11/1994 | Pinchuk ................................. 604/27 |
| 5,364,340 | 11/1994 | Coll .......................................... 604/8 |
| 5,364,344 | 11/1994 | Beattie et al. ........................... 604/43 |
| 5,366,464 | 11/1994 | Belknap ................................. 606/159 |
| 5,372,600 | 12/1994 | Beyar et al. . |
| 5,374,245 | 12/1994 | Marhurkar .............................. 604/43 |
| 5,378,230 | 1/1995 | Marhurkar .............................. 604/43 |
| 5,380,270 | 1/1995 | Ahmadzadeh . |
| 5,380,276 | 1/1995 | Miller et al. ............................ 604/28 |
| 5,384,928 | 1/1995 | Scott et al. . |
| 5,391,196 | 2/1995 | Devonec . |
| 5,395,316 | 3/1995 | Martin ..................................... 604/43 |
| 5,399,172 | 3/1995 | Martin et al. ......................... 604/248 |
| 5,401,257 | 3/1995 | Chevalier, Jr. et al. ............. 604/265 |
| 5,403,291 | 4/1995 | Abrahamson ........................ 604/280 |
| 5,405,320 | 4/1995 | Twardowski et al. ................. 604/43 |
| 5,405,329 | 4/1995 | Durand ................................. 604/164 |
| 5,405,341 | 4/1995 | Martin ................................... 604/284 |
| 5,405,380 | * 4/1995 | Gianotti et al. ...................... 623/1.11 |
| 5,411,490 | 5/1995 | Tennican et al. ..................... 604/236 |
| 5,440,327 | 8/1995 | Stevens ................................... 346/46 |
| 5,449,372 | * 9/1995 | Schmaltz et al. .................... 606/198 |
| 5,451,206 | 9/1995 | Young .................................... 604/43 |
| 5,464,398 | 11/1995 | Haindl .................................. 604/280 |
| 5,470,322 | 11/1995 | Horzewski et al. ................. 604/280 |
| 5,472,417 | 12/1995 | Martin et al. ........................... 604/43 |
| 5,472,432 | 12/1995 | Martin ................................... 604/248 |
| 5,480,380 | 1/1996 | Martin ..................................... 604/43 |
| 5,486,159 | 1/1996 | Maharkur ................................. 604/4 |
| 5,489,278 | 2/1996 | Abrahamson ........................ 604/280 |
| 5,509,897 | 4/1996 | Twardowski et al. ................. 604/43 |
| 5,514,100 | 5/1996 | Marhurkar ............................ 604/195 |
| 5,514,176 | 5/1996 | Bosley, Jr. . |
| 5,514,178 | 5/1996 | Torchio . |
| 5,520,697 | 5/1996 | Lindenberg et al. . |
| 5,522,807 | 6/1996 | Luther .................................. 604/264 |
| 5,527,337 | 6/1996 | Stack et al. ........................... 606/198 |
| 5,531,741 | 7/1996 | Barbacci ................................ 606/15 |
| 5,540,713 | 7/1996 | Schnepp-Pesch et al. . |
| 5,554,136 | 9/1996 | Luther .................................. 604/264 |
| 5,556,390 | 9/1996 | Hicks .................................... 604/280 |
| 5,562,641 | 10/1996 | Flomenbilt et al. . |
| 5,569,182 | 10/1996 | Twardowski et al. ................. 604/43 |
| 5,569,184 | 10/1996 | Crocker et al. ......................... 604/53 |
| 5,569,195 | 10/1996 | Saab ........................................ 604/96 |
| 5,571,093 | 11/1996 | Cruz et al. ............................ 604/270 |
| 5,573,508 | 11/1996 | Thornton ................................. 604/96 |
| 5,599,291 | 2/1997 | Balbierz et al. ......................... 604/8 |
| 5,613,980 | 3/1997 | Chauhan ............................... 606/194 |
| 5,624,413 | 4/1997 | Markel et al. ........................ 604/280 |
| 5,630,794 | 5/1997 | Lax et al. ................................ 604/22 |
| 5,639,278 | 6/1997 | Dereume et al. . |
| 5,643,222 | 7/1997 | Marhurkar ............................ 604/195 |
| 5,647,843 | 7/1997 | Mesrobian et al. ...................... 604/8 |
| 5,649,909 | 7/1997 | Cornelius ................................ 604/96 |
| 5,653,689 | 8/1997 | Buelna et al. ........................... 604/96 |
| 5,667,486 | 9/1997 | Mikulich et al. . |
| 5,674,277 | 10/1997 | Freitag . |
| 5,676,697 | 10/1997 | McDonald . |
| 5,681,274 | 10/1997 | Perkins et al. ........................... 604/8 |
| 5,683,640 | 11/1997 | Miller et al. ......................... 264/255 |
| 5,685,862 | 11/1997 | Marhurkar ............................ 604/194 |
| 5,685,867 | 11/1997 | Twardowski et al. ............... 604/280 |
| 5,695,479 | 12/1997 | Jagpal .................................. 604/264 |
| 5,707,386 | 1/1998 | Schnepp-Pesch et al. . |
| 5,766,209 | 6/1998 | Devonec . |
| 5,769,868 | 6/1998 | Yock ..................................... 604/194 |
| 5,776,161 | 7/1998 | Globerman . |
| 5,792,105 | 8/1998 | Lin et al. ................................ 604/96 |
| 5,792,400 | 8/1998 | Talja et al. . |
| 5,795,326 | 8/1998 | Simán .................................... 604/43 |
| 5,830,179 | 11/1998 | Mikus et al. . |
| 5,830,184 | 11/1998 | Basta .................................... 604/104 |
| 5,830,196 | 11/1998 | Hicks .................................... 604/280 |
| 5,843,028 | 12/1998 | Weaver et al. ......................... 604/54 |
| 5,860,999 | 1/1999 | Schnepp-Pesch et al. . |
| 5,866,815 | 2/1999 | Tihon . |
| 5,876,417 | 3/1999 | Devonec et al. . |
| 5,906,640 | 5/1999 | Penn et al. . |
| 5,928,217 | 7/1999 | Mikus et al. . |
| 5,964,771 | 10/1999 | Beyar et al. . |
| 6,033,413 | 3/2000 | Mikus et al. . |
| 6,139,536 | 10/2000 | Mikus et al. . |

FOREIGN PATENT DOCUMENTS 41 03 573 A     8/1992     (DE) .

| | | |
|---|---|---|
| 41 34 030 A | 4/1993 | (DE) . |
| 93 14 585 | 1/1994 | (DE) . |
| 0036642 A2 | 9/1981 | (EP) . |
| 0079719 A1 | 5/1983 | (EP) . |
| 0101890 B1 | 3/1984 | (EP) . |
| 0144525 A2 | 6/1985 | (EP) . |
| 0168136 A1 | 1/1986 | (EP) . |
| 0183421 A2 | 6/1986 | (EP) . |
| 0101890 A1 | 9/1986 | (EP) . |
| 0 326 908 A | 8/1989 | (EP) . |
| 0333308 A2 | 9/1989 | (EP) . |
| 0183421 B1 | 4/1990 | (EP) . |
| 0386408 A1 | 9/1990 | (EP) . |
| 0490459 A1 | 6/1992 | (EP) . |
| 0490459 B1 | 6/1992 | (EP) . |
| 0554722 A | 8/1993 | (EP) . |
| 0 876 803 | 11/1998 | (EP) . |
| 1285953 | 1/1962 | (FR) . |
| 1508959 | 12/1967 | (FR) . |
| 2297640 A1 | 8/1976 | (FR) . |
| 2530958 A1 | 2/1984 | (FR) . |
| 2611486 | 9/1988 | (FR) . |
| 2017499 A | 10/1979 | (GB) . |
| 2156220 A | 10/1985 | (GB) . |
| 2235384 A | 3/1991 | (GB) . |
| 57-90150 | 6/1982 | (JP) .............................. A51M/25/00 |
| 62-20830 | 8/1994 | (JP) . |
| WO 84/04043 | 10/1984 | (WO) . |
| WO 95/26763 | 10/1995 | (WO) . |
| WO 9710858 | 3/1997 | (WO) . |
| WO 97/17094 | 5/1997 | (WO) . |
| WO 97/37699 | 10/1997 | (WO) . |
| WO 97/37718 | 10/1997 | (WO) . |

OTHER PUBLICATIONS

MEDCOMP Catalog "Schon Twin–Cath" (date unknown).
Quinton Instrument Co. Catalog, "Hemodialysis and Apheresis" (1994).
Quinton Instrument Co. Catalog, "Hemodialysis and Apheresis" (1995).
Quinton Instrument Co. Catalog, "Oncology/Critical Care" (1993).
Risenfeld, et al. "Surface Modification of Functionally Active Heparin," Medical Device Technology (Mar. 1995).
"Triple Lumen Catheter" p. 3 (First? An Information Service of Individual, Inc., Sep. 25, 1995).
Bard/angiomed product brochure, 1988.
Bard brochure, "Introducing The Bard Urinary Diversion Stent," 1984.
Bard product brochure, "Introducing The Bard Pediatric Urethral Stent," 1983.
Bard product brochure, "Stents To Satisfy The Urologist . . . ", 1988.
Bard Urological Division product catalog, 1990, (pp. 1–3, A1–A30, D7–D26; last page).
Bigongiari et al., "Conversion of Percutaneous Ureteral Stent To Indwelling Pigtail Stent Over Guidewire," Urology, May 1980, vol. XV, No. 5, (pp. 461–465).
Birch et al., "Tethered Ureteric Stents—a Clinical Assessment," British Journal of Urology, 1988, vol. 62, (pp. 409–411).
Camacho et al. "Double–Ended Pigtail Ureteral Stent: Useful Modification to Single End Ureteral Stent," Urology, May 1979, vol. XIII, No. 5, (pp. 516–520).
Collier et al., "Proximal Stent Displacement As Complication of Pigtail Ureteral Stent," Urology, Apr. 1979, vol. XIII, No. 4, (pp. 372–375).
Cook Urological catalog, "Urological Surgical Products," 1990–1991, (pp. 1–3, 7–29, 48–148; last page).
Cook Urological product brochure, "Ureteral Stents," 1987, (pp. 1–23; last page).
Cook Urological Catalog, 1995, (pp. 1–2, 9–41, 63–173; last page).
Cook Urological product brochure, "Filiform Ureteral Multi–Length Silicone Stent Sets," 1989.
Culkin, "Complications of Ureteral Stents," Infections in Urology, Sep./Oct. 1996, (pp. 139, 142–143).
Hackethorn et al., "Antegrade Internal Ureteral Stenting: A Technical Refinement," Radiology, Jul. 1985, vol. 156, No. 3, (pp. 827–828).
Hepperlen et al., "Self–Retained Internal Ureteral Stents: A New Approach," The Journal of Urology, Jun. 1978, vol. 119, (pp. 731–734).
Mardis, "Evaluation of Polymeric Materials for Endourologic Devices," Seminars in Interventional Radiology, Mar. 1987, vol. 4, No. 1, (pp. 36–45).
Mardis et al., "Double Pigtail Ureteral Stent," Urology, Jul. 1979, vol. XIV, No. 1, (pp. 23–26).
Mardis et al., "Comparative Evaluation of Materials Used for Internal Ureteral Stents," Journal of Endourology, 1993, vol. 7, No. 2, (pp. 105–115).
Mardis et al., "Guidewires, Ureteral Catherters, and Stents," Color Atlas/Text of Ureteroscopy, 1993 New York, Igaku–Shoin, Ch. 5, (pp. 65–84).
Mardis et al., "Polyethylene Double–Pigtail Ureteral Stents," Urologic Clinics of North America, Feb. 1982, vol. 9, No. 1, (pp. 95–101).
Mardis et al., "Ureteral Stents Use and Complications," Problems in Urology, Jun. 1992 vol. 6, No. 2, (pp. 296–306).
Mardis et al., "Ureteral Stents–Materials," Urologic Clinics of North America, Aug. 1988, vol. 15, No. 3, (pp. 471–479).
Minkov et al., "Our Experience in the Application of the Biocompatible Indwelling Ureteral Stents", International Urology and Nephrology, 1986, 18 (4), (pp. 403–409).
Rutner et al., "Percutaneous Pigtail Nephrostomy," Urology, Oct. 1979, vol. XIV, No. 4, (pp. 337–340).
Sadlowski et al., "New Technique For Percutaneous Nephrostomy Under Ultrasound Guidance," Journal of Urology, May 1979, vol. 121, (pp. 559–561).
Stables, "Percutaneous Nephrostomy: Techniques, Indications, and Results," Urologic Clinics of North America, Feb. 1982, vol. 9, No. 1, (pp. 15–19).
Surgitek brochure, "The Solution Is Perfectly Clear," 1990.
"Ureteroscopic Procedures—Technical Advances," Color Atlas/Text of Ureteroscopy, 1993 New York, Igaku–Shoin, p. 281.

* cited by examiner

MEDICAL DEVICE WITH ONE OR MORE HELICAL COILS

TECHNICAL FIELD

The invention generally relates to stents with one or more helical coils at one end. More specifically, the invention relates to such stents and their use and manufacture.

BACKGROUND INFORMATION

Fluid sometimes needs to be drained from a body. For example, urine formed in one or both kidneys might need to be drained into the bladder. One way to accomplish such drainage is to use a medical device that conveys the fluid (e.g., urine) through a lumen. Such devices include stents and catheters. Existing stents can be uncomfortable for the patient, especially when they reside in the ureter between the kidney and the bladder. Moreover, known stents can lead to retention of bodily fluids. For example, oftentimes a stricture develops in the ureter due to irritation of the ureter by the placed stent, thereby blocking urine flow from the kidney into the bladder and leading to retention of urine in the kidney.

SUMMARY OF THE INVENTION

The present invention allows for fluid drainage while both maintaining patient comfort and preventing fluid retention resulting from the presence of the fluid-draining device in the body.

In one aspect, the present invention relates to a medical device comprising a first elongated section having a first cross-sectional area and a second elongated section having a second cross-sectional area. The second elongated section extends from the first elongated section, and the second cross-section area is smaller than the first cross-sectional area. The second elongated section includes at least one coiled structure that has a plurality of turns (e.g., a regular helix or an irregular helix). One advantage of this aspect of the invention is, for example, that the smaller cross-sectional area of the second elongated section increases patient comfort. A second advantage of this aspect of the invention is, for example, that the coiled structure with the plurality of turns allows fluids (e.g., urine) to flow under conditions in which a body stricture would prevent urine flow if a known stent was used in the body.

Embodiments of this aspect of the invention may include the following features. For example, the first elongated section can be a conduit defining a lumen and having a proximal segment and a distal segment. Also, the plurality of turns can define a passageway that extends through the plurality of turns and along an axis about which the turns are wound. The coiled structure can be a piece of solid material that is wound to form the plurality of turns. The lumen defined by the conduit and the passageway defined by the turns of the coiled structure can be in communication. The distal segment can be configured to allow the device to be retained within a part of the body, and the proximal segment may be an elongated structure. All or a portion of the conduit may have openings (e.g., apertures, holes and/or pores) which communicate with a lumen defined within the conduit. The coiled structure can be flexible and/or resilient, and it can be made of a material that is flexible and/or resilient. The first and second elongated sections can extend along a longitudinal axis. In some embodiments, the device includes two or more of the coiled structures. One particular embodiment of the device has two coiled structures each of which has a helical shape. Medical devices according to the invention may be, for example, a stent and/or a ureteral drainage stent.

In another aspect, the invention involves a placement method where a device, such as the medical device described above, is placed in a body to allow fluid drainage.

In yet another aspect, the invention relates to a method of manufacturing such a device.

BRIEF DESCRIPTION OF THE DRAWINGS

In the drawings, like reference characters generally refer to the same parts throughout the different views. Also, the drawings are not necessarily to scale, emphasis instead generally being placed upon illustrating principles of the invention.

DESCRIPTION

The invention relates to medical devices (e.g., stents) for draining fluids and to methods for placing and making such devices. The invention increases patient comfort and prevents fluid retention if a stricture in a vessel develops. For simplicity and illustrative purposes, the invention is described here in the context of draining urine from a kidney, through a ureter, and into the bladder. However, the invention is applicable to any situation that requires drainage within a body, from a body, and from one body structure to another. One such situation is, for example, biliary drainage from the gall bladder, through the biliary ducts, to the duodenum.

Generally, a device according to the invention has a first elongated section and a second elongated section. The first elongated section typically has two segments, a more proximal segment and a more distal segment. Proximal, in this case, refers to that end of the stent which, during placement, is relatively closer to the physician (or other medical professional) than the other end of the stent (the distal end). The second elongated section typically is one or more elongated coiled structures having a plurality of turns. The plurality of turns define a passageway that extends through the plurality of turns and along an axis about which the turns are wound. The coiled structure may be, for example, a regular helical shape (e.g., with regularly spaced turns and/or a constant diameter of the passageway) or an irregular helical shape (e.g., with irregularly spaced turns and/or a passageway with a cross-sectional area that varies over the length of the passageway). The cross-sectional area of the second elongated section is smaller than the cross-sectional area of the first elongated section.

Each coiled structure allows fluid to pass through the passageway defined by the plurality of turns, drain along the surface of the coiled structure, and flow between the spaces between the plurality of turns. One way fluid movement is caused is, for example, by a wicking and/or capillary action.

Figure 3:
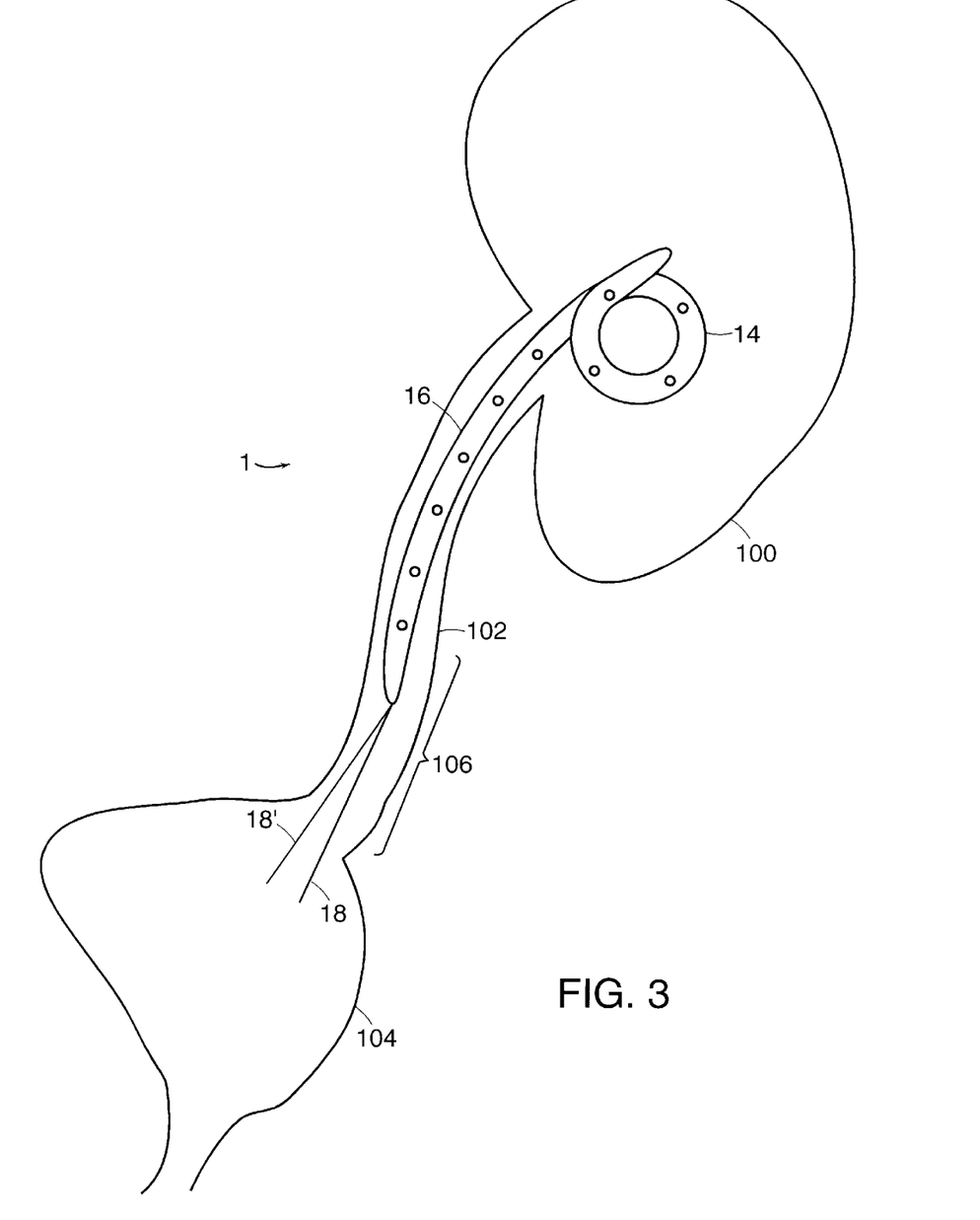
FIG. 3 shows the device of FIGS. 1A, 1B, 2A, and 2B placed within the body of a patient, specifically within the kidney, ureter, and bladder of the patient.

In some embodiments, the distal segment has a structure which retains the device within the kidney (or other body structure). The proximal segment resides within at least a portion of the ureter. At some point along and within the ureter, the first elongated section transitions to the second elongated section. The elongated coiled structure(s) of the second elongated section generally reside within a proximal portion of the ureter (i.e., the portion of the ureter that is closer to the bladder than to the kidney). Also, the elongated coiled structure(s) may extend out of the ureter and into the bladder. For example, the stent 1 of FIG. 3 is positioned in the manner described above.

Figure 1A:
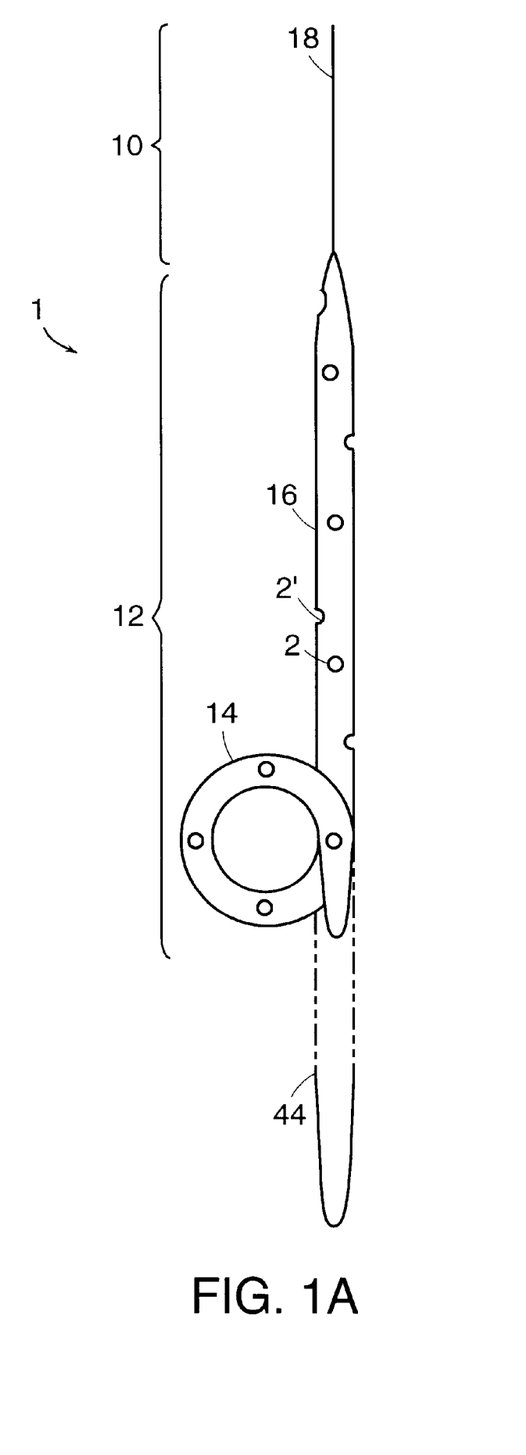
FIG. 1A shows a side view of one embodiment of a medical device according to the invention.
Figure 1B:
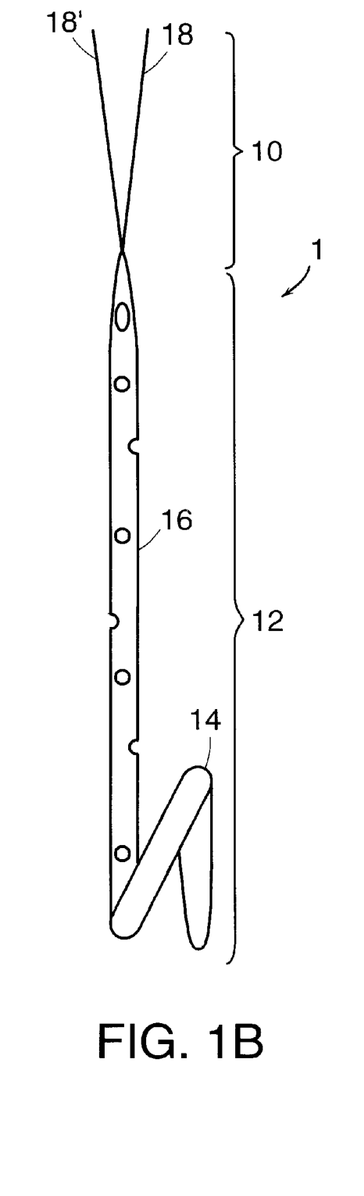
FIG. 1B shows a view of the device of FIG. 1A, but rotated 90 degrees from the orientation shown in FIG. 1A.

Referring to FIG. 1A, in one embodiment of a medical device according to the invention, a stent 1 has a first elongated section 12 with a distal segment 14 and a proximal segment 16. The distal segment 14 is shown having one of a variety of possible configurations that serve to retain the stent 1 in the kidney. As depicted, in this embodiment, the distal segment 14 is a curl. The curl completes slightly more than one revolution of a circle. Additionally, the curl winds around and extends along an axis which is perpendicular to the proximal segment 16 (FIG. 1B). In general, any structure of the distal segment 14 that serves to retain one end of the stent 1 in the kidney is a suitable.

The first elongated section 12 is shown with openings 2, 2' which may be, for example, holes, pores, or apertures (for the sake of clarity, only two openings 2, 2' are designated specifically). The openings 2, 2' communicate with a lumen defined by the wall of the first elongated section 12. The first elongated section 12 extends to the second elongated section 10 which has two coiled structures 18, 18' (FIG. 1B). The first elongated section 12 has a first cross-sectional area and the second elongated section 10 has a second cross-sectional area; the second cross-sectional area is less than the first cross-sectional area. The second cross-sectional area, in one embodiment, refers to the cross-sectional area of one of the coiled structures, and in another embodiment, refers to the total cross-sectional area of all of the coiled structures when taken together. These coiled structures 18, 18', which have a smaller cross-sectional area than the first elongated section 12, allow greater patient comfort because of their relatively small diameter.

Figure 2A:
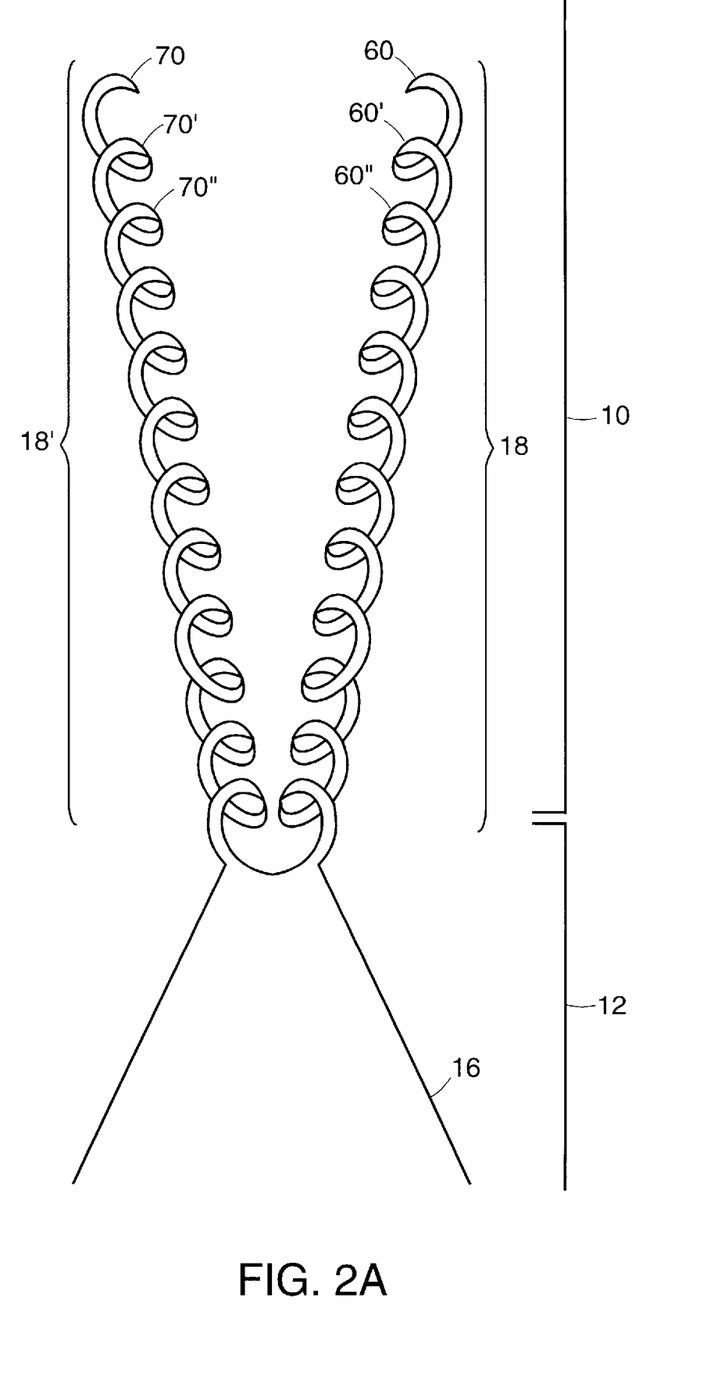
FIG. 2A shows an enlarged view of one section of the device of FIGS. 1A and 1B.

An enlargement of the stent 1 shows the transition from the first elongated section 12 to the second elongated section 10 (FIG. 2A). The proximal segment 16 transitions into the two coiled structures 18, 18'. Each coiled structure 18, 18' has a plurality of turns (e.g., 60, 60', 60" and 70, 70', 70", respectively). Only a portion of the plurality of turns are labeled for the sake of clarity. The transition between the first elongated section and the second elongated section is characterized by single-piece construction. A single piece of material forms the first and second elongated sections. Also, the proximal segment 16 narrows (i.e., its cross-sectional area decreases) as the first section 12 transitions to the second section 10. In alternative embodiments, two or more pieces of one or more materials may be joined to form a medical device of the invention. Additionally, the proximal segment 16 may remain constant in cross-sectional area along its length up to and including the transition between the first and second sections.

Figure 2B:
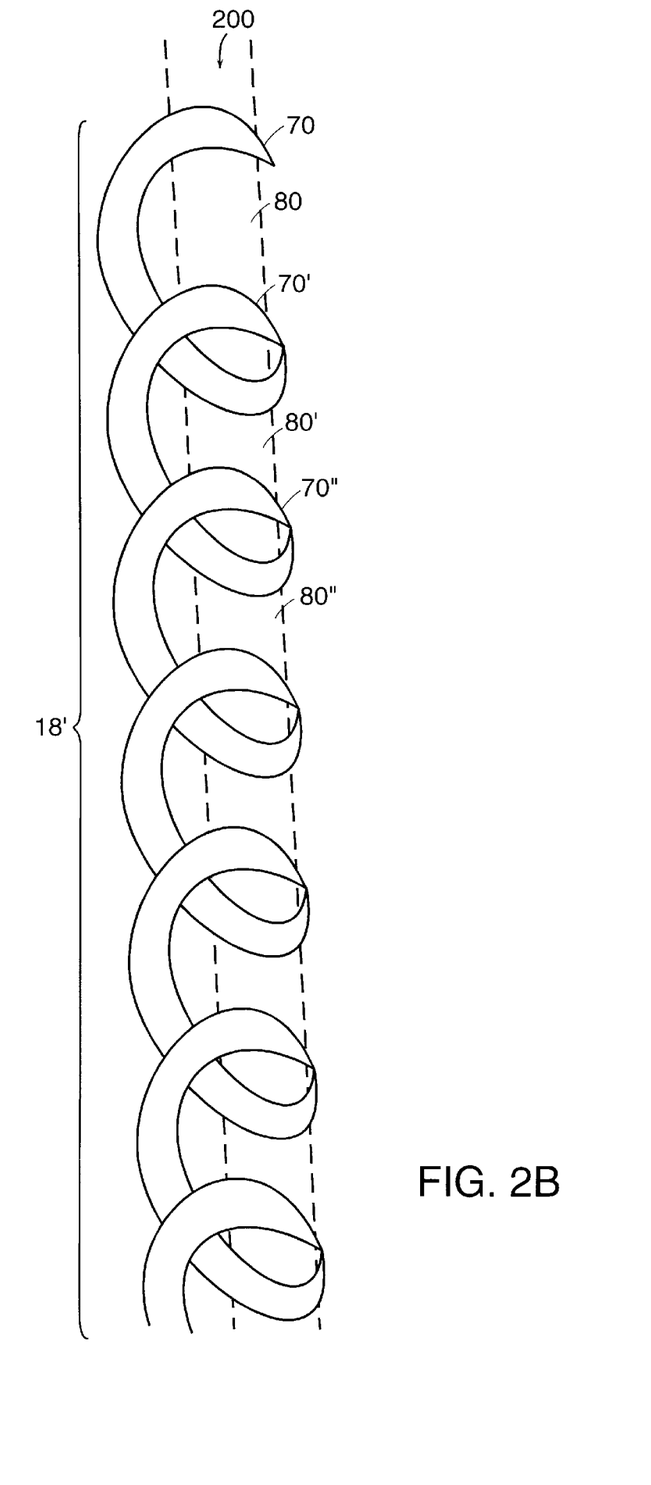
FIG. 2B shows an enlarged view of one coiled structure of the device of FIGS. 1A, 1B, and 2A.

A further enlargement of the stent 1 shows one of the coiled structures 18' in detail (FIG. 2B). Schematically represented with dashed lines is a passageway 200 defined by the plurality of turns 70, 70', 70." The dashed lines are not meant to define the limits of the passageway 200, but rather to indicate generally where the passageway is located in relation to the plurality of turns.

Medical devices according to the invention including the embodiment shown in FIG. 2B allow fluid to pass through the passageway 200, drain along the surface of the coiled structure 18', and flow between the spaces 80, 80', 80" (not all spaces are labeled for the sake of clarity) between the plurality of turns. This movement of fluid may be caused, for example, by a wicking and/or capillary action.

This wicking/capillary action is similar to that which occurs with the tails disclosed in U.S. Ser. No. 08/743,885 by Clayman et al. (the "Clayman device"). However, an advantage of medical devices according to the invention over the Clayman device is, for example, that even if a stricture were to form around the coiled structure (in, for example, a ureter), some fluid still could pass through at least the passageway of the coiled structure.

Taking a step back, strictures are characterized by a narrowing of the lumen of a vessel in the body, for example, a narrowing of a portion the lumen of a ureter. Cancer and/or trauma to the vessel wall, for example, may cause swelling and/or constrictions of the vessel. This swelling and/or constriction ultimately may narrow the lumen of the vessel, forming a stricture.

Medical devices according to the invention prevent fluid from being retained behind the site of the stricture (e.g., in the ureter and kidney) while, at the same time, maintain patient comfort. Even when a stricture forms, a coiled structure of the invention, with a passageway which is formed by a plurality of turns and which is capable of passing a significant amount of urine, allows urine to flow. Thus, the coiled structure prevents urine retention in the ureter and/or kidney. A second elongated section with multiple coiled structures particularly is useful because, not only can fluid pass through a stricture via the passageway formed by the plurality of turns in any of the coiled structures, but the turns of the coiled structures are not easily compressed. Thus, the lumen is maintained in a more fully open state than would be a simple conduit with solid walls. Moreover, the stricture cannot easily squeeze together the multiple coiled structures themselves. The multiple coiled structures prop open the vessel at the stricture, to a degree. These benefits allow urine to pass around, along, and through the coiled structures, even in the event of a stricture.

In certain embodiments of medical devices according to the invention, the first elongated section may have, for example, a circular cross-section. The circular cross-section may be of any circumference that is of suitable size for the body structure into which the device is placed. For example, for use in the kidney, ureter, and bladder, a first elongated section or a portion of the first elongated section may be from about 8.0 french to about 4.8 french in size. The first elongated section may have a constant cross-sectional area along its length. Alternatively, the first elongated section may be tapered from about the distal end to about the proximal end with the size of the section decreasing from about 7 french to about 3 french. Other french sizes and tapering configurations are useful depending upon either the average size in a population or the actual size in an individual of the body structure or structures into which the device is placed.

Medical devices according to the invention may be constructed from any of a number of materials. Those materials that are useful include, for example, materials that are able to flex but also retain their shape, to a degree, when they are perturbed. Additionally, useful materials are, for example, materials that have a resilient quality, being able to regain at least some of their original shape when the stent ceases to be perturbed and/or resist, for example, compression. One such material that combines these features is Percuflex™. Moreover, thermo-formable materials, including, for example, Percuflex™ are useful in the practice of the invention.

Some embodiments of the invention allow fluids and/or solids dissolved in fluids to move between the environment into which the device is placed and the internal space defined by the walls and or plurality of turns of the device. For example, in certain embodiments, the first elongated section may contain openings such as apertures, holes, or pores that allow fluids to pass through the wall of the device. These openings may be of any size that allows fluids to pass through the wall effectively. In other embodiments, the first elongated section may have walls which allow fluids to pass osmotically.

Referring to FIG. 3, the stent 1 is placed within a kidney 100, a ureter 102, and a bladder 104. The distal segment 14 resides within the kidney 100. The curled shape of the distal segment 14 retains the stent within the kidney 100. As previously described, the curl completes slightly more than one revolution of a circle and winds around and extends along an axis which is perpendicular to the proximal segment 16. The proximal segment 16 extends from the distal segment 14 and resides within the ureter 102. The first elongated section 12 transitions into the second elongated section 10 in the proximal portion of the ureter 106. The second elongated section 10 has two coiled structures 18, 18' that extend into the bladder 104. The second elongated section 10 need not transition from the first elongated section 12 to the second elongated section 10 in the proximal ureter 106. For example, the transition may occur anywhere along the ureter 102.

In operation, the distal end of the first elongated section 12 is inserted through the bladder 104 and ureter 102 into the kidney 100. As shown in FIG. 1A, the distal segment 14 may be straightened 44. Once the distal segment is in a straightened position 44, the stent 1 is inserted through the bladder 104 and ureter 102 into the kidney 100. One manner to straighten the first elongated section 12 is to produce relative movement between a straightening device (e.g., a sheath) and the first elongated section 12, such that the straightening device moves distally relative to the first elongated section 12, thereby uncurling the distal segment to the straightened position 44. Once at least some portion of the distal segment 14 is positioned within the kidney 100, the straightening device is removed. The first elongated section 12 is constructed from a shape-memory material. Thus, once the straightening device is withdrawn, the distal segment in a straightened position 44 returns to its curled shape.

An alternative method to straighten the curl of the distal segment 14 is to use a guidewire which slides along the stent 1 and is sufficiently stiff to hold the curl in a straight configuration (e.g., the distal segment in a straightened position 44, FIG. 1A) when it is placed alongside that portion of the distal segment 14. Relative movement is produced between the guidewire and the first elongated section 12, such that the guidewire moves distally relative to the first elongated section 12, thereby uncurling the distal segment to the straightened position 44. Once at least a portion of the distal segment 14 is positioned within the kidney 100, the guidewire is withdrawn. The shape-memory material from which the first elongated section 12 is constructed allows the distal segment in a straightened position 44 to return to its curled shape once the guidewire is withdrawn. Other modes of inserting and/or straightening a device also are useful.

Figure 4:
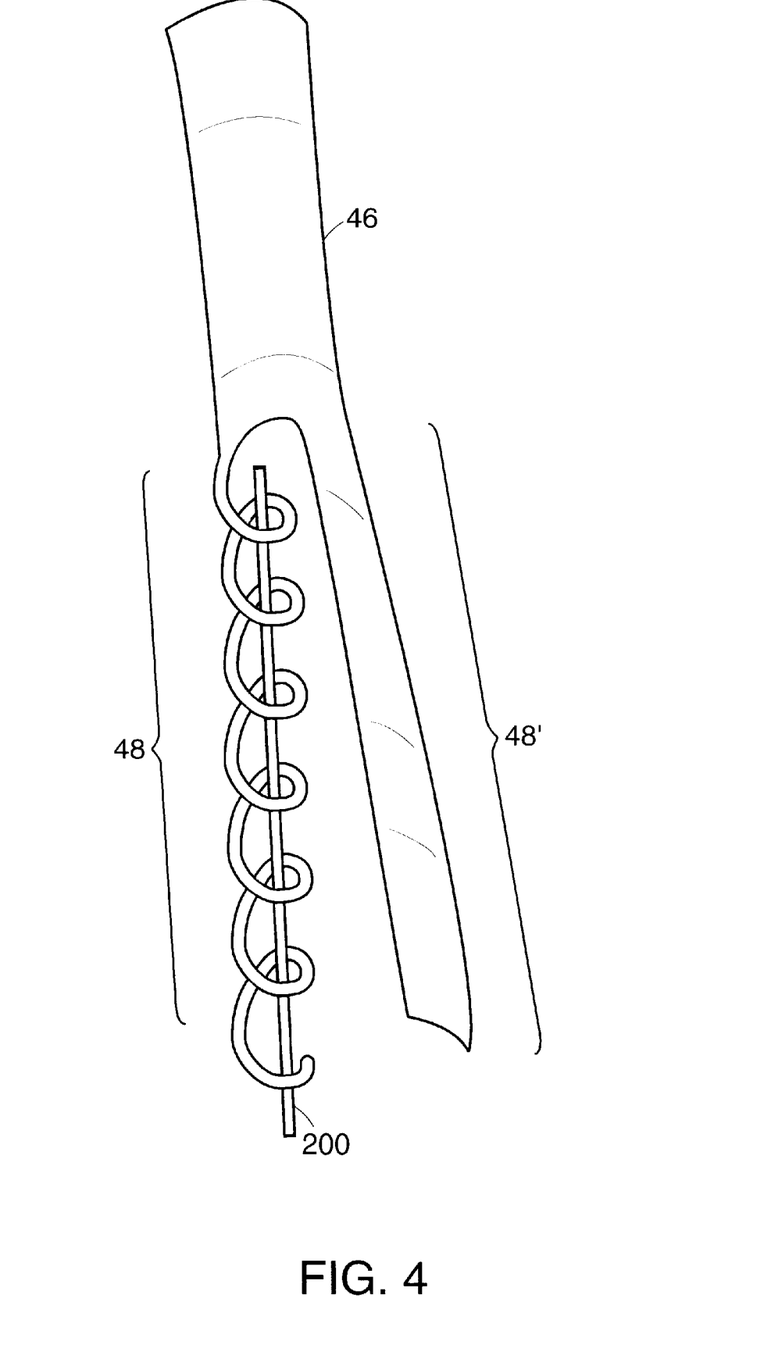
FIG. 4 illustrates a way to manufacture a device according the invention.

Referring to FIG. 4, one method of manufacturing medical devices according to the invention is to section a conduit 46 lengthwise by slicing the wall of the conduit 46. For example, the wall of the conduit is sliced at positions that are on either end of a diameter of the conduit 46. Two portions 48, 48' are formed. One of the portions 48 is wrapped around a form 200, for example, a mandrel or a steel wire. The portion 48 may be heated, for example, in hot water, in order to set the portion 48 in an elongated coiled configuration.

However, any number of portions may be formed when the conduit is sectioned lengthwise, and any number of portions may be wrapped around a form and set into an elongated coiled configuration. For example, the wall of the conduit may be cut longitudinally at one point. This single portion can be wrapped around a form and set into an elongated coiled configuration. Alternatively, the wall of the conduit may be cut longitudinally at a plurality of points. Some or all of the resulting portions may be wrapped around a form and set into an elongated coiled configuration. Additionally, some of the portions which result from sectioning the conduit lengthwise may be removed entirely or partially.

Another manner of manufacturing a device of the invention may be, for example, to join a first elongated section with a second elongated section that has previously been manufactured to contain a structure or structures in an elongated coiled configuration.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A medical device for draining fluid, comprising:
   (A) a first elongated section having a first cross-sectional area and comprising a tubular proximal section generally extending along an axis, the proximal section in connection with a distal section, the distal section comprising a curl offset from the axis; and
   (B) a second elongated section having a second cross-sectional area and extending from the first elongated section, the second cross-sectional area being smaller than the first cross-sectional area and the second elongated section comprising two or more non-concentric coiled structures, at least two of the two or more coiled structures each having a plurality of turns.

2. The medical device of claim 1 wherein the proximal section defines a lumen.

3. The medical device of claim 2 wherein the plurality of turns of at least one of the at least two of the two or more coiled structures defines a passageway extending through the plurality of turns of the at least one of the at least two of the two or more coiled structures.

4. The medical device of claim 3 wherein the at least one of the at least two of the two or more coiled structures comprises a piece of solid material that is wound to form the plurality of turns of at least one of the at least two of the two or more coiled structures.

5. The medical device of claim 3 wherein the lumen communicates with the passageway.

6. The medical device of claim 1 wherein the distal segment comprises a retaining structure.

7. The medical device of claim 1 wherein the proximal segment comprises an elongated structure.

8. The medical device of claim 1 wherein the first section has at least one opening in a wall.

9. The medical device of claim 1 wherein at least one of the two or more coiled structures comprises a flexible material.

10. The medical device of claim 1 wherein the first and second elongated sections extend along a longitudinal axis.

11. The medical device of claim 1 wherein the medical device comprises a stent.

12. The medical device of claim 1 wherein the medical device comprises a ureteral drainage stent.

13. The medical device of claim 1 wherein at least one of the two or more coiled structures comprises a resilient material.

* * * * *

UNITED STATES PATENT AND TRADEMARK OFFICE
CERTIFICATE OF CORRECTION

PATENT NO.    : 6,332,892 B1
DATED         : December 25, 2001
INVENTOR(S)   : Desmond, III et al.

It is certified that error appears in the above-identified patent and that said Letters Patent is hereby corrected as shown below:

<u>Column 6,</u>
Line 67, replace "segment" with -- section --.

<u>Column 7,</u>
Line 2, replace "segment" with -- section --.

Signed and Sealed this

Twelfth Day of August, 2003

JAMES E. ROGAN
*Director of the United States Patent and Trademark Office*